United States Patent [19]

Perouse

[11] Patent Number: 5,792,156
[45] Date of Patent: Aug. 11, 1998

[54] INSTRUMENT FOR VASCULAR SURGERY AND ITS USE

[75] Inventor: Eric Perouse, L'Isle Adam, France

[73] Assignee: Laboratoire Perouse Implant, Bornel, France

[21] Appl. No.: 671,222

[22] Filed: Jun. 27, 1996

[30] Foreign Application Priority Data

Jun. 27, 1995 [FR] France .................. 95 07730

[51] Int. Cl.$^6$ .......................... A61B 17/00; A61M 29/00
[52] U.S. Cl. .................. 606/159; 604/96; 606/194
[58] Field of Search .................. 606/159, 191, 606/198, 200; 604/104

[56] References Cited

U.S. PATENT DOCUMENTS

| | | |
|---|---|---|
| 4,650,466 | 3/1987 | Luther . |
| 4,885,003 | 12/1989 | Hillstead . |
| 5,190,058 | 3/1993 | Jones et al. . |
| 5,405,380 | 4/1995 | Gianotti et al. . |
| 5,490,859 | 2/1996 | Mische et al. ............... 606/159 |

FOREIGN PATENT DOCUMENTS

| | | |
|---|---|---|
| 0 375 775 | 7/1990 | European Pat. Off. . |
| 0 518 704 | 12/1992 | European Pat. Off. . |
| 0 567 788 | 11/1993 | European Pat. Off. . |
| 31 07 392 | 9/1982 | Germany . |
| 94/24946 | 11/1994 | WIPO . |

*Primary Examiner*—Michael Powell Buiz
*Assistant Examiner*—William W. Lewis
*Attorney, Agent, or Firm*—Wenderoth, Lind & Ponack, L.L.P.

[57] ABSTRACT

An instrument for vascular surgery includes a deformable cylindrical sleeve whose proximal end is integral with a distal end of a sheath and whose distal end is integral with a distal and of a catheter contained in the sheath. The sleeve can pass from a contracted state to a dilated state, and vice versa, by exerting a reciprocating movement on the catheter in relation to the sheath. The sleeve is made up of a latticework embedded in an envelope. This instrument can be used for the dilation or temporary occlusion of a blood vessel, or for performing an embolectomy.

8 Claims, 2 Drawing Sheets

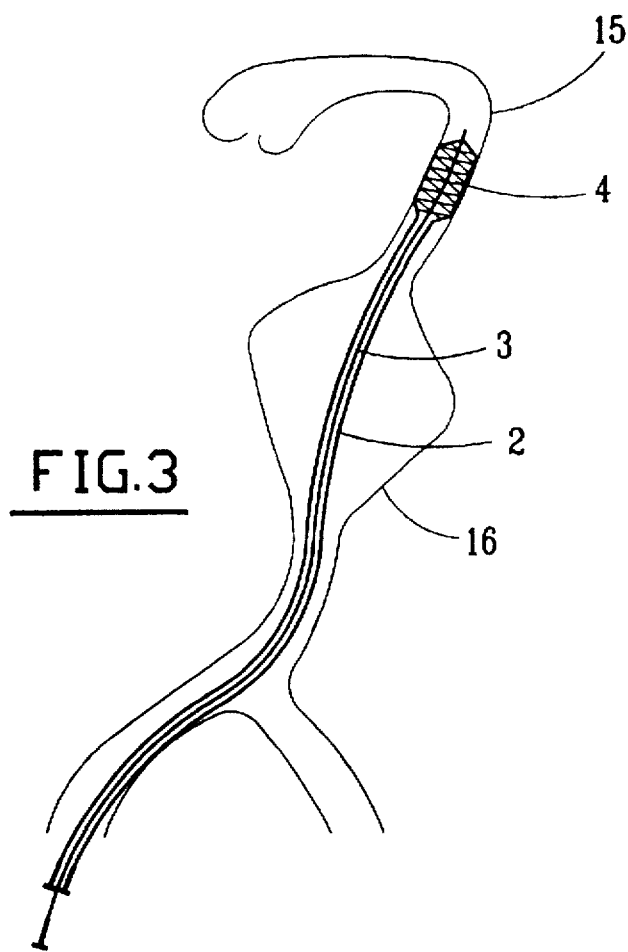
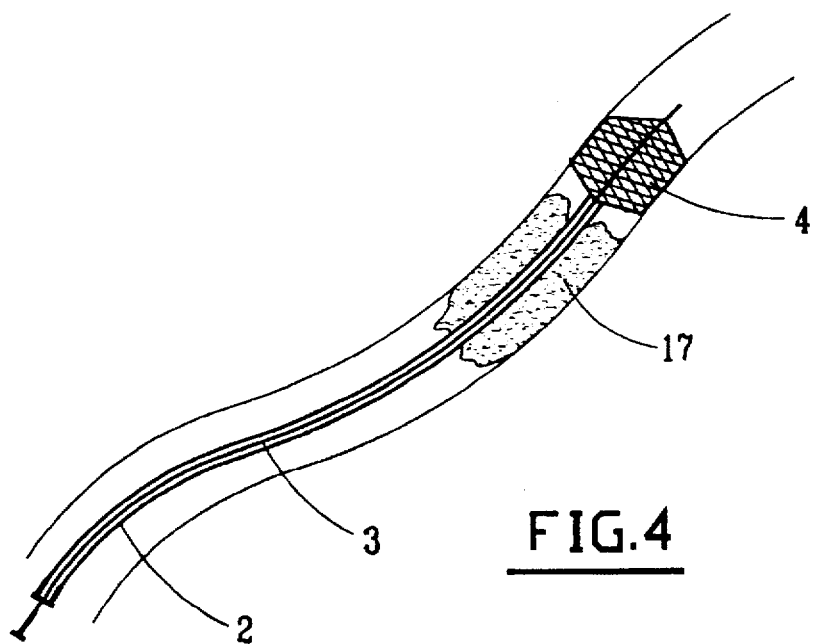

INSTRUMENT FOR VASCULAR SURGERY AND ITS USE

BACKGROUND AND SUMMARY OF THE INVENTION

The present invention relates to an instrument for vascular surgery.

The object of an invention is to make available an economical and reliable instrument for vascular surgery which can be employed for different uses during several types of surgical operations, for example as an instrument for performing an embolectomy, or else as an instrument for dilation or temporary occlusion of vessels.

To this end, the invention relates to an instrument for vascular surgery comprising an elongated sheath, a catheter extending through said sheath and a dilatable and contractable sleeve having an intermediate substantially cylindrical portion, a proximal end portion integral with a distal end of a sheath, and a distal end portion integral with a distal end of said catheter, the sleeve being able to pass from a contracted state to a dilated state, and vice versa, by exerting a reciprocating movement on the catheter relative to the sheath, the sleeve comprising a latticework which is completely embedded in an envelope made of an extensible material, the sleeve forming a volume including an intermediate tubular sheet in said intermediate portion and two sheets, namely one proximal sheet and one distal sheet, which close off said volume and are connected to the distal ends of the sheath and of the catheter, respectively, through said proximal and distal end portions, respectively.

The invention also relates to the use of such an instrument in one or other of the aforementioned applications.

BRIEF DESCRIPTION OF THE DRAWINGS

Illustrative embodiments of the invention will now be described with reference to the attached drawings, in which:

FIGS. 3 and 4 are longitudinal crosssections of a vessel in which an instrument according to the invention is inserted.

DETAILED DESCRIPTION OF THE INVENTION

Figure 1:
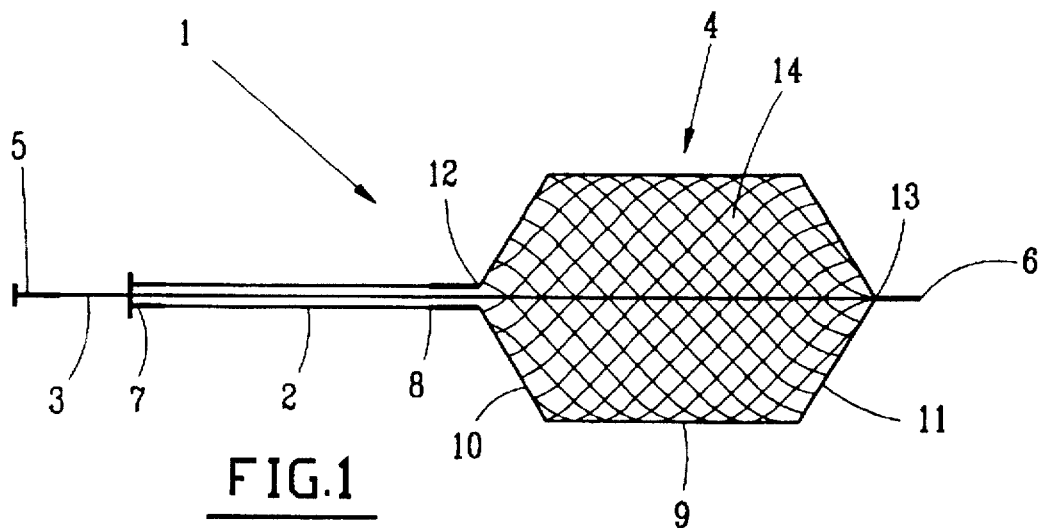
FIG. 1 is a side view of an instrument for vascular surgery according to the invention, shown in a dilated state.

The instrument 1 for vascular surgery represented in FIG. 1 is made up of a sheath 2, a catheter 3 and an expandable sleeve 4.

The catheter 3, whose length is greater than that of the sheath 2, is inserted into sheath 2 in such a way that its proximal end 5 and distal end 6 extend on either side beyond the proximal end 7 and distal end 8 of the sheath 2.

The catheter 3 and the sheath 2 are made of plastic and/or metal materials which are resistant to buckling.

The sleeve 4 is made from a tubular latticework which is formed by circular weaving of filaments, which are of identical length and are made of stainless steel of biocompatible quality. These filaments thus form regular meshes distributed on a central sheet 9 constituting the cylindrical body of the sleeve 4, while the ends of these filaments are joined together in such a way as to form two sheets, namely a proximal sheet 10 and a distal sheet 11, thereby defining the proximal end 12 and the distal end 13 of the sleeve 4. These sheets, of convergent shape, close off the volume of this sleeve.

The proximal end 12 of the sleeve is fixed to the distal end 8 of the sheath 2, and the distal end 13 of this sleeve is integral with the distal end 6 of the catheter 3.

Figure 2:
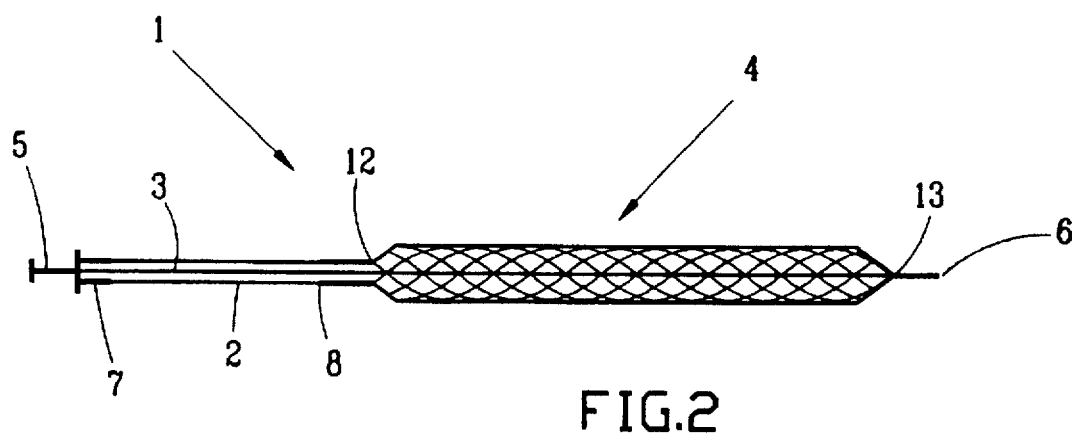
FIG. 2 is a side view of the instrument in FIG. 1, but shown in the contracted state.

In order to deform this sleeve, that is to say in order to vary its diameter, the catheter 3 is imparted a reciprocating movement in relation to the sheath 2. The distal end 13 of the sleeve 4 is thus moved away from or moved towards the proximal end 12 of sleeve 4, allowing the latter to pass from a contracted state (FIG. 2) to a dilated state (FIG. 1) and vice versa.

The difference in length between the catheter 3 and the sheath 2 is such that in the contracted state the diameter of the sleeve 4 is very small compared to its length (FIG. 2), and of the same order as that of the sheath 2.

Moreover, the latticework is completely embedded in an envelope or film 14 made of leakproof extensible material, such as a biocompatible elastomer, capable of following the deformations of the meshes without tearing and without detaching from the latticework.

The instrument which has just been described can be used as an instrument for temporary dilation of a vessel. This instrument is in this case inserted in its contracted state into a vessel until the sleeve reaches the zone of the vessel to be dilated. The instrument passes from its contracted state to its dilated state by means of a pulling movement being exerted on the catheter while the sheath 2 is held stationary.

In order to facilitate the insertion of the instrument into the vessels, the contracted state of the sleeve preferably corresponds to its state of rest. It is not therefore necessary to exert any action on the catheter when it is being put into place.

This instrument can also be used as a device for temporary occlusion of a vessel (FIG. 3). In its dilated state, it makes it possible to temporarily block the vessel 15 in which it is placed, so as to permit, for example, operation on a downstream aneurysm 16.

The function of this instrument is comparable to that of a balloon, but it has the advantage of attaining a precise diameter, which is easy to determine, of being rapidly deflated, and of being at no risk of bursting. Moreover, the latticework of the sleeve 4 does not risk pinching the arterial tissues. Nevertheless, in the dilated state, the length of the sleeve 4 must be considerable in order to ensure a firm impaction in the vessel. For this purpose, it suffices to create a latticework in which the number of turns is sufficient.

The instrument can also be used as an embolectomy probe (FIG. 4) in order to remove a clot from a vessel. The instrument is passed in its contracted state through a thrombus 17, it is then dilated behind the latter, and, finally, the wall of the artery is scraped by pulling the instrument rearwards.

It may sometimes be advantageous for the meshes of the proximal sheet 10 to be irregular. The lengths of the filaments constituting the latticework as well as their points of attachment on the periphery of the proximal end 12 of the sleeve 4 are chosen judiciously for this purpose.

It should be noted that the instrument according to the present invention has a very simple structure and at the same time can be used during different types of surgical operations.

I claim:

1. An instrument for vascular surgery, said instrument comprising:

an elongated sheath;

a catheter extending through said sheath;

a dilatable and contractable sleeve having an intermediate substantially cylindrical portion, a proximal end portion integral with a distal end of said sheath, and a distal end portion integral with a distal end of said catheter, said sleeve being able to pass from a contracted state to a dilated state, and vice versa, by exerting a reciprocating movement on said catheter relative to said sheath; and said sleeve comprising a latticework which is completely embedded in an envelope made of an extensible material, said sleeve forming a volume including an intermediate tubular sheet in said intermediate portion and a proximal sheet and a distal sheet which close off said volume and which are connected to said distal ends of said sheath and of said catheter, respectively, through said proximal and distal and portions, respectively.

2. An instrument according to claim 1, wherein meshes of said latticework in said distal sheet and in said proximal sheet of said sleeve have substantially the same area.

3. An instrument according to claim 1, wherein meshes of said proximal sheet of said sleeve are of substantially different areas from one another, and meshes of said distal sheet of said sleeve are of substantially the area, the smallest meshes of said proximal sheet having substantially the same area as said meshes of said distal sheet.

4. An instrument according to claim 1, wherein said sleeve, in said contracted state, has an outer diameter of the same order as an outer diameter of said sheath.

5. An instrument for vascular surgery, said instrument comprising:

an elongated sheath;

a catheter extending through said sheath;

a dilatable and contractable sleeve having an intermediate substantially cylindrical portion, a proximal end portion integral with a distal end of said sheath, and a distal end portion integral with a distal end of said catheter, said sleeve being able to pass from a contracted state to a dilated state, and vice versa, by exerting a reciprocating movement on said catheter relative to said sheath; and said sleeve comprising a latticework which is completely embedded in an envelope made of a liquid-tight extensible material, said sleeve forming a volume including an intermediate tubular sheet in said intermediate portion and a proximal sheet and a distal sheet which close off said volume and which are connected to said distal ends of said sheath and of said catheter, respectively, through said proximal and distal end portions, respectively.

6. An instrument according to claim 5, wherein meshes of said latticework in said distal sheet and in said proximal sheet of said sleeve have substantially the same area.

7. An instrument according to claim 5, wherein meshes of said proximal sheet of said sleeve are of substantially different areas from one another, and meshes of said distal sheet of said sleeve are of substantially the same area, the smallest meshes of said proximal sheet having substantially the same area as said meshes of said distal sheet.

8. An instrument according to claim 5, wherein said sleeve, in said contracted state, has an outer diameter of the same order as an outer diameter of said sheath.

* * * * *